US00PP20066P2

(12) United States Plant Patent
Oliver

(10) Patent No.: US PP20,066 P2
(45) Date of Patent: Jun. 9, 2009

(54) ***HEUCHERA* PLANT NAMED 'RASPBERRY CHIFFON'**

(50) Latin Name: *Heuchera×hybrida*
Varietal Denomination: Raspberry Chiffon

(76) Inventor: Charles Oliver, 921 Scottsdale-Dawson Rd., Scottsdale, PA (US) 15683

( * ) Notice: Subject to any disclaimer, the term of this patent is extended or adjusted under 35 U.S.C. 154(b) by 0 days.

(21) Appl. No.: 12/154,223

(22) Filed: May 21, 2008

(51) Int. Cl.
*A01H 5/00* (2006.01)

(52) U.S. Cl. ..... Plt./440

(58) Field of Classification Search ..... Plt./440
See application file for complete search history.

*Primary Examiner*—Annette H Para
(74) *Attorney, Agent, or Firm*—C. A. Whealy

(57) ABSTRACT

A new and distinct cultivar of *Heuchera* plant named 'Raspberry Chiffon', characterized by its full, densely foliated and uniformly mounded plant habit; vigorous growth habit; ruffled purple bronze and silver-colored leaves; numerous large light pink-colored flowers arranged on erect panicles; and excellent garden performance.

2 Drawing Sheets

Botanical designation: *Heuchera×hybrida.*
Cultivar denomination: 'Raspberry Chiffon'.

BACKGROUND OF THE INVENTION

The present invention relates to a new and distinct cultivar of *Heuchera,* botanically known as *Heuchera×hybrida* and hereinafter referred to by the name 'Raspberry Chiffon'.

The new *Heuchera* is a product of a planned breeding program conducted by the Inventor in Scottdale, Pa. The objective of the breeding program is to create new vigorous *Heuchera* cultivars with uniform plant habit, and attractive leaf and flower coloration.

The new *Heuchera* originated from a cross-pollination made by the Inventor in May, 2000 in Scottdale, Pa. of *Heuchera* 'Pearl Pendants', not patented, as the female, or seed, parent with a proprietary selection of *Heuchera* identified as code number H99-9B, not patented, as the male, or pollen, parent. The new *Heuchera* was discovered and selected by the Inventor as a single flowering plant within the progeny of the stated cross-pollination in a controlled greenhouse environment in Scottdale, Pa. in June, 2001.

Asexual reproduction of the new *Heuchera* by cuttings in a controlled greenhouse environment in Scottdale, Pa. since October, 2001, has shown that the unique features of this new *Heuchera* are stable and reproduced true to type in successive generations.

SUMMARY OF THE INVENTION

The new *Heuchera* has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Raspberry Chiffon'. These characteristics in combination distinguish 'Raspberry Chiffon' as a new and distinct cultivar of *Heuchera:*

1. Full, densely foliated and uniformly mounded plant habit.
2. Vigorous growth habit.
3. Ruffled purple bronze and silver-colored leaves.
4. Numerous large light pink-colored flowers arranged on erect panicles.
5. Excellent garden performance.

Plants of the new *Heuchera* differ from plants of the female parent, 'Pearl Pendants', in the following characteristics:

1. Leaves of plants of the new *Heuchera* are more deeply lobed than leaves of plants of 'Pearl Pendants'.
2. Leaves of plants of the new *Heuchera* are more ruffled than leaves of plants of 'Pearl Pendants'.
3. Plants of the new *Heuchera* and 'Pearl Pendants' differ in leaf color as plants of 'Pearl Pendants' have bronze green-colored leaves.

Plants of the new *Heuchera* differ from plants of the male parent selection in the following characteristics:

1. Leaves of plants of the new *Heuchera* are more deeply lobed than leaves of plants of the male parent selection.
2. Leaves of plants of the new *Heuchera* are more ruffled than leaves of plants of the male parent selection.
3. Plants of the new *Heuchera* and the male parent selection differ in leaf color as plants of the male parent selection have grey green-colored leaves.

Plants of the new *Heuchera* can be compared to plants of the *Heuchera* 'Harmonic Convergence', disclosed in U.S. Plant Pat. No. 11,111. In side-by-side comparisons conducted in Scottdale, Pa., plants of the new *Heuchera* differed from plants of 'Harmonic Convergence' in the following characteristics:

1. Leaves of plants of the new *Heuchera* were smaller, more deeply lobed and more ruffled than leaves of plants of 'Harmonic Convergence'.
2. Plants of the new *Heuchera* had shorter and narrower inflorescences than plants of 'Harmonic Convergence'.
3. Plants of the new *Heuchera* had larger flowers than plants of 'Harmonic Convergence'.

BRIEF DESCRIPTION OF THE PHOTOGRAPHS

The accompanying colored photographs illustrate the overall appearance of the new *Heuchera,* showing the colors as true as it is reasonably possible to obtain in colored reproductions of this type. Colors in the photographs may differ slightly from the color values cited in the detailed botanical description which accurately describe the colors of the new *Heuchera.*

The photograph on the first sheet comprises a side perspective view of a typical plant of 'Raspberry Chiffon'.

The photograph on the second sheet is a close-up view of typical flowers of 'Raspberry Chiffon'.

DETAILED BOTANICAL DESCRIPTION

The aforementioned photographs and following observations, measurements and values describe plants grown in Scottdale, Pa. in one-gallon containers in a glass-covered greenhouse and under conditions which closely approximate commercial *Heuchera* production. During the production of the plants, day temperatures ranged from 15° C. to 26° C. and night temperatures ranged from 5° C. to 15° C. Plants were one year old when the photographs and the description were taken. In the description, color references are made to The Royal Horticultural Society Colour Chart, 1995 Edition, except where general terms of ordinary dictionary significance are used.

Botanical classification: *Heuchera×hybrida* 'Raspberry Chiffon'.

Parentage:

*Female, or seed, parent.*—*Heuchera×hybrida* 'Pearl Pendants', not patented.

*Male, or pollen, parent.*—Proprietary selection of *Heuchera×hybrida* identified as code number H99-9B, not patented.

Propagation:

*Type.*—By cuttings.

*Time to initiate roots, summer.*—About 15 days at 23° C.

*Time to initiate roots, winter.*—About 21 days at 17° C.

*Time to produce a rooted young plant, summer.*—About 45 days at 23° C.

*Time to produce a rooted young plant, winter.*—About 60 days at 17° C.

*Root description.*—Fine, fibrous; white in color.

*Rooting habit.*—Freely branching; moderately dense.

Plant description:

*Appearance.*—Herbaceous perennial; basal rosette plant habit with leaves developing from the base; densely foliated; full, mounded and uniform plant habit with upright panicles with white-colored flowers. Vigorous growth habit.

*Plant size.*—Height, soil level to top of foliar plane: About 10 cm. Height, soil level to top of panicles: About 60 cm. Diameter or spread: About 30 cm.

Foliage description:

*Arrangement.*—Basal rosette, simple.

*Length.*—About 9 cm.

*Width.*—About 9.5 cm.

*Shape.*—Rounded cordate; seven-lobed.

*Apex.*—Broadly obtuse, lobed.

*Base.*—Auriculate.

*Margin.*—Crenate with ciliation; ruffled.

*Texture, upper and lower surfaces.*—Slightly pubescent; slightly rough.

*Venation pattern.*—Palmate; reticulate.

*Color.*—Developing and fully expanded leaves, upper surface: Close to 198A; venation, close to 131A underlain with close to 200A. Developing and fully expanded leaves, lower surface: Close to 187A; venation, 187A.

*Petiole.*—Length: About 12 cm. Diameter: About 1.8 mm. Texture, upper and lower surfaces: Smooth. Color, upper and lower surfaces: Close to 187B.

Flower description:

*Appearance/arrangement.*—Single campanulate flowers arranged on loose, narrow and mostly erect panicles; about ten to 15 panicles develop during the flowering season, each panicle with about 150 to 250 flowers and flower buds. Flowers face mostly outward to slightly downward. Flowers not fragrant.

*Time of flowering.*—Plants flower from May through August in Scottdale, Pa.; flowering continuous during this period.

*Inflorescence longevity.*—Individual inflorescences last about one week on the plant. Flowers persistent.

*Inflorescence size.*—Length: About 40 to 60 cm. Diameter: About 7 cm.

*Flower size.*—Diameter: About 5 mm. Depth (height): About 9 mm.

*Flower buds.*—Height: About 4 mm. Diameter: About 2.5 mm. Shape: Bulbous. Color: Close to 59C.

*Sepals.*—Quantity/arrangement: Five sepals; radially symmetrical and fused at base. Calyx length: About 7 mm. Calyx diameter: About 5 mm. Shape: Elongate. Apex: Obtuse. Margin: Entire. Texture, upper and lower surfaces: Pubescent. Color, upper surface: Close to 62D; towards the apex, shaded with close to 150D. Color, lower surface: Close to 155D; shaded with close to 59D; glandular hairs, close to 59B; towards the apex, shaded with close to 150D.

*Petals.*—Quantity/arrangement: Five minute petals; radially symmetrical. Length: About 4 mm. Width: About 2 mm. Shape: Spatulate. Apex: Acute. Margin: Serrate. Texture, upper surface: Smooth, glabrous. Texture, lower surface: Glandular hairs. Color, upper surface: Close to 62D. Color, lower surface: Close to 62D; glandular hairs, close to 62A.

*Flower bracts.*—Length: About 4 mm. Width: About 1 mm. Shape: Lanceolate. Apex: Acute. Margin: Serrate. Texture, upper and lower surfaces: Glandular hairs. Color, upper and lower surfaces: Close to 187B.

*Peduncles.*—Strength: Strong. Aspect: Mostly erect to about 30° from vertical. Length: About 20 cm to 25 cm. Diameter: About 2 mm. Texture: Pubescent. Color: Close to 187B.

*Pedicels.*—Strength: Strong. Aspect: About 30° from vertical. Length: About 2 mm. Diameter: About 0.2 mm. Texture: Pubescent. Color: Close to 187B.

*Reproductive organs.*—Androecium: Stamen number: Five per flower. Anther shape: Oval. Anther size: About 1 mm by 0.6 mm. Anther color: Close to 25B. Amount of pollen: Moderate. Pollen color: Close to 25B. Gynoecium: Pistil number: Two per flower. Pistil length: About 6 mm. Stigma shape: Round. Stigma color: Close to 157A. Style length: About 5 mm. Style color: Close to 157D. Ovary color: Close to 157D.

*Seed.*—Size: About 0.6 mm by 0.3 mm. Color: Close to 202A.

Disease/pest resistance: Resistance to pathogens and pests common to *Heuchera* has not been observed on plants grown under commercial conditions.

Garden performance: Plants of the new *Heuchera* have been observed to have excellent garden performance. Plants of the new *Heuchera* have demonstrated good tolerance to rain, wind, night temperatures as low as −30° C. and day temperatures as high as 45° C.

It is claimed:

1. A new and distinct *Heuchera* plant named 'Raspberry Chiffon' as illustrated and described.

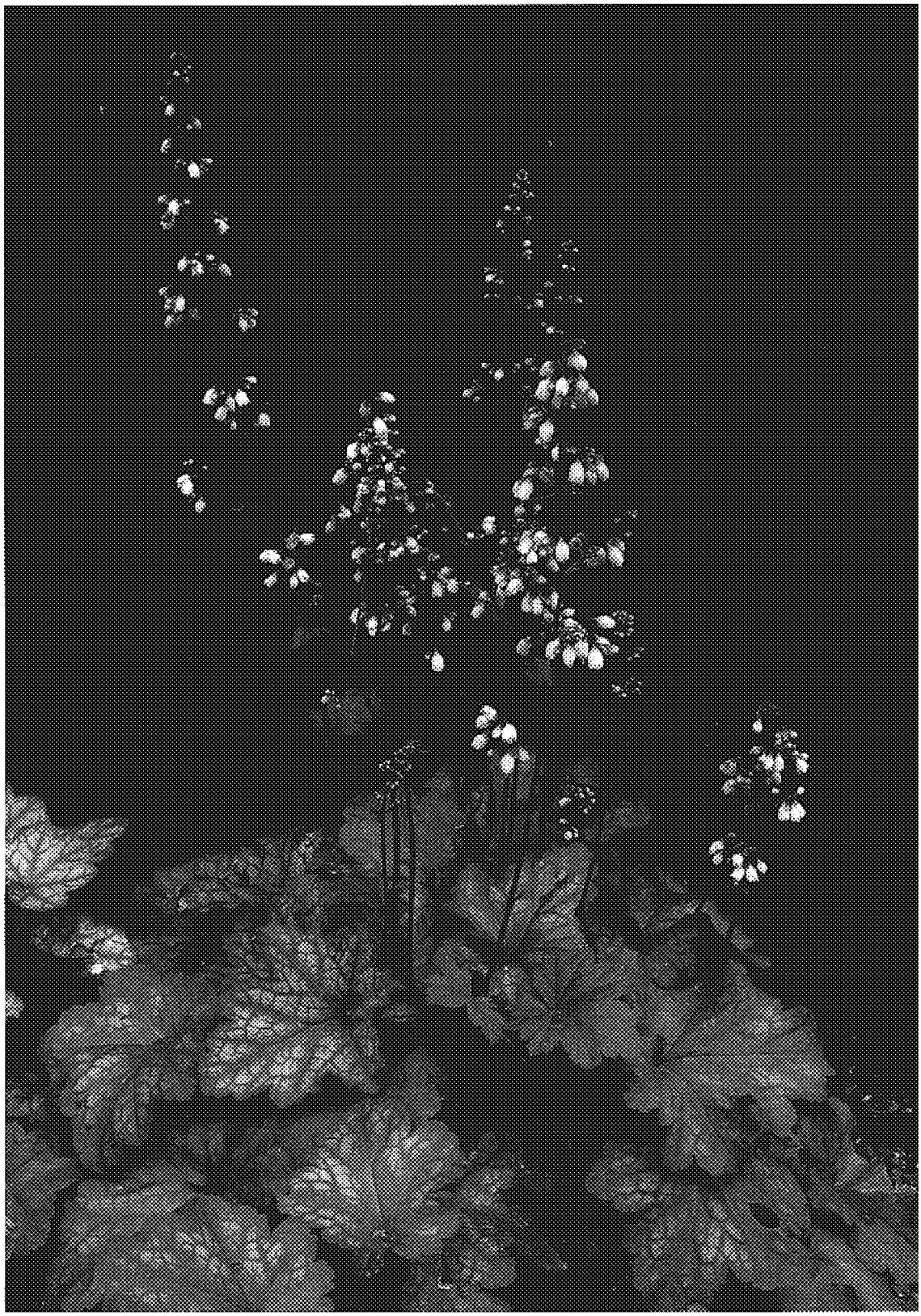

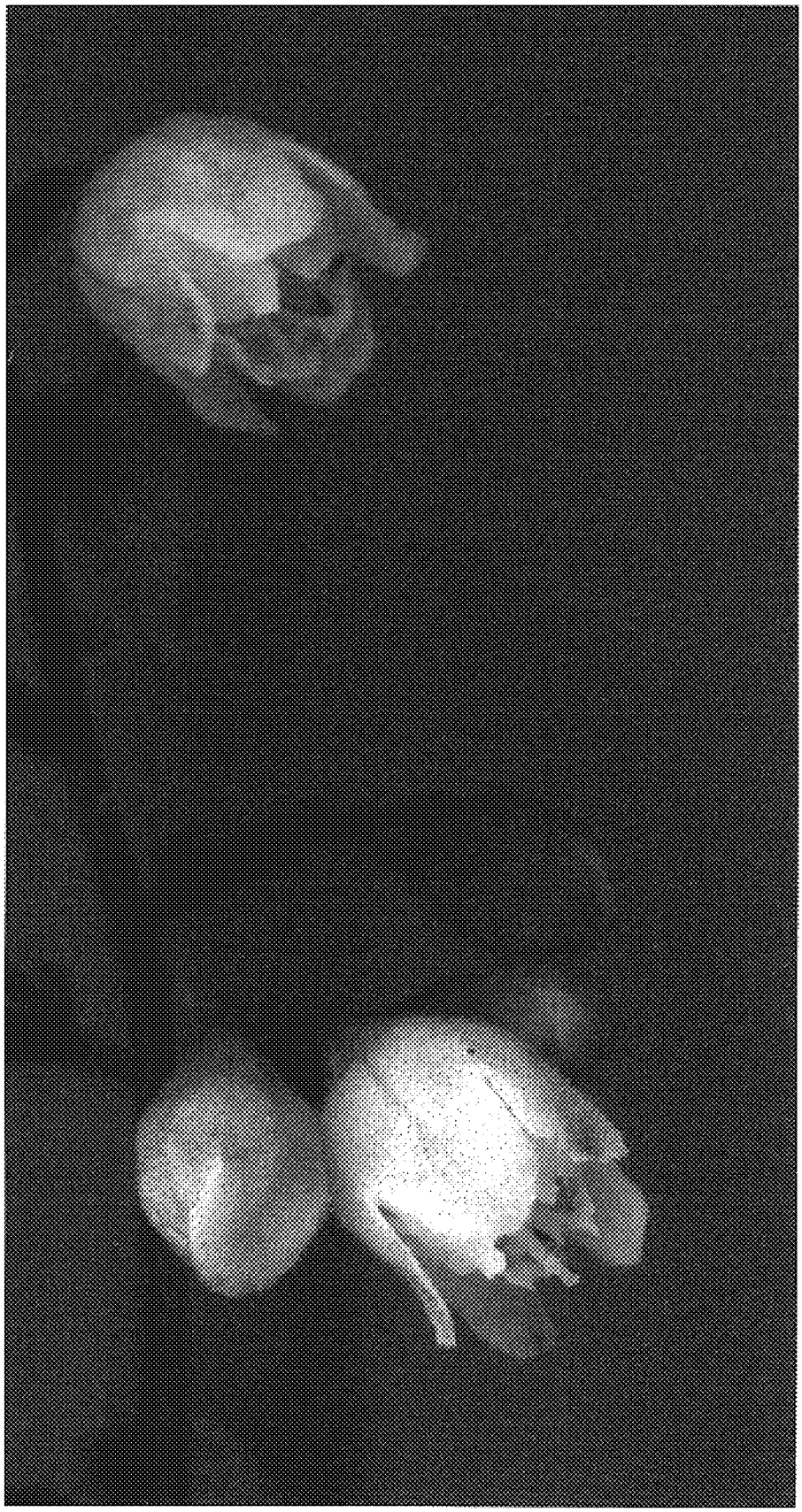

* * * * *